United States Patent [19]

Yafuso et al.

[11] Patent Number: 5,296,381
[45] Date of Patent: Mar. 22, 1994

[54] SENSING ELEMENTS AND METHODS FOR MAKING AND USING SAME

[75] Inventors: Masao Yafuso, El Toro, Calif.; Paul F. Korkowski, Hastings; Roger A. Mader, Stillwater, both of Minn.; Cheng Yan, Irvine, Calif.; John T. Carlock, Powell, Ohio

[73] Assignee: Minnesota Mining & Manufacturing Co., St. Paul, Minn.

[21] Appl. No.: 742,002

[22] Filed: Aug. 8, 1991

[51] Int. Cl.⁵ .......................................... G01N 21/64
[52] U.S. Cl. ............................... 436/172; 422/55; 422/58; 422/82.07; 422/82.08; 436/68; 528/10
[58] Field of Search ............... 436/68, 172; 422/55, 422/58, 57, 82.07, 82.08; 528/10, 15, 30–32, 43

[56] References Cited

U.S. PATENT DOCUMENTS

| | | | |
|---|---|---|---|
| Re.31,879 | 5/1985 | Lubbers et al. | 436/133 |
| 3,612,866 | 10/1971 | Stevens . | |
| 3,725,658 | 4/1973 | Stanley et al. . | |
| 4,041,932 | 8/1977 | Fostick . | |
| 4,194,877 | 3/1980 | Peterson . | |
| 4,468,229 | 8/1984 | Su | 8/507 |
| 4,548,907 | 10/1985 | Seitz et al. | 436/163 |
| 4,557,900 | 12/1985 | Heitzmann | 422/55 |
| 4,657,736 | 4/1987 | Marsoner et al. | 422/56 |
| 4,712,865 | 12/1987 | Hsu et al. | 8/523 |
| 4,714,770 | 12/1987 | Hsu et al. | 8/523 |
| 4,746,751 | 5/1988 | Oviatt, Jr. et al. | 8/506 |
| 4,746,751 | 5/1988 | Oviatt, Jr. et al. | 8/506 |
| 4,775,514 | 10/1988 | Barnikol et al. | 422/55 |
| 4,798,738 | 1/1989 | Yafuso et al. | 427/2 |
| 4,824,789 | 4/1989 | Yafuso et al. | 436/68 |
| 4,840,485 | 7/1989 | Gratton | 356/317 |
| 4,849,172 | 7/1989 | Yafuso et al. | 422/55 |
| 4,867,919 | 9/1989 | Yafuso et al. | 264/1.5 |
| 4,900,933 | 2/1990 | Nestor et al. | 250/458.1 |
| 4,916,160 | 4/1990 | Boardman et al. | 522/27 |
| 4,929,561 | 5/1990 | Hirschfeld | 436/116 |
| 5,015,715 | 5/1991 | Divers et al. | 528/15 |
| 5,019,350 | 5/1991 | Rhum et al. | 422/82.07 |
| 5,037,615 | 8/1991 | Kane | 422/82.08 |

FOREIGN PATENT DOCUMENTS

| | | |
|---|---|---|
| 2009024 | 8/1990 | Canada . |
| 2105415 | 10/1990 | Canada . |
| 0109959 | 5/1984 | European Pat. Off. . |
| 0283206 | 9/1988 | European Pat. Off. . |
| 0363219 | 4/1990 | European Pat. Off. . |
| 0368481 | 5/1990 | European Pat. Off. . |
| 0381026 | 8/1990 | European Pat. Off. . |
| 0413114 | 2/1991 | European Pat. Off. . |
| 0413499 | 2/1991 | European Pat. Off. . |
| 0442276A1 | 8/1991 | European Pat. Off. . |
| 106086 | 5/1974 | Fed. Rep. of Germany . |
| WO8805533 | 7/1988 | PCT Int'l Appl. . |
| 2132348A | 7/1984 | United Kingdom . |

OTHER PUBLICATIONS

Berlman et al., On the fluorescence spectrum and decay time of naphthalene, Mol. Phys. 5,313(1962).

Yanari et al, Fluorescence of Styrene Hompolymers and Copolymers, Nature, 1963, vol. 200.

Fumio Hirayama, Intramolecular Excimer Formation. I. Diphenyl and Triphenyl Alkanes, The Journal of Chemical Physics, vol. 42, No.9, 1965.

Kroneis et al, A Fluorescence-Based Sterilizable Oxygen Probe For Use in Bioreactors, Sensors and Actuators, 4(1983)587–592.

(List continued on next page.)

*Primary Examiner*—Jill A. Johnston
*Attorney, Agent, or Firm*—Gordon L. Peterson; Frank J. Uxa, Jr.

[57] ABSTRACT

A sensing element for sensing the concentration of an analyte in a medium is disclosed. The sensing element comprises a matrix material having at least one indicator component covalently bonded thereto. The indicator component is capable of providing a signal dependent on the concentration of a analyte in a medium. The indicator component is derived from at least one indicator compound having an aromatic ring to which is directly bonded a group including a functional portion which is conjugated relative to this aromatic ring.

39 Claims, 1 Drawing Sheet

OTHER PUBLICATIONS

Sharma et al, Unusually Efficient Quenching of the Fluorescence of an Energy Transfer-Based Optical Sensor for Oxygen, Analytica Chimica Acta, 212(1988) 261–265.

Hui, et al, An Accurate, Low-Cost, Easily-Manufacturable Oxygen Sensor, SPIE vol. 1172 Chemical, Biochemical, and Environmental Sensors (1989) pp. 233–238.

Barton et al, Organosilicon Chemistry, 1990 American Chemical Society.

Wolfbeis, Otto, Oxygen Sensors, Fiber Optic Chemical Sensors and Biosensors, vol. II, 19–53,1991.

Wolfbeis, Otto, Appendix: A Selection of Relevant Patents, vol. I,17–2.1991, Fiber Optic Chemical Sensors and Biosensors.

Wolfbeis, Otto, VIII. Internal Referencing, and IX Rejection of Interfering Light, Fiber Optic Chemical Sensors & Biosensors, vol.1, 102–110,1.

Lakowicz, Joseph R., Spectral Characteristics of Systems Which Undergo a Reversible Two-State Reaction, Principles of Fluorescence Spectroscopy, 1983, 383–429.

Ueno et al, Host-Guest Sensory Systems for Detecting Organic Compounds by Pyrene Excimer Fluoroscence, Anal. Chem. 1990,62,2461–2456.

Lee et al, Luminescence Ratio Indicators for Oxygen, Anal. Chem. 1987, 59,279–283.

W. Ware, Oxygen Quenching of Fluoroscence in Solution: An Experimental Study of the Diffusion Process, 1962, vol. 66,455–458.

Cherkasov et al, Excited Dimers(Excimers) of Anthracene Derivatives and Concentration Quenching of Fluorescence, Akad Nauk USSR Bull Phys. Science, 29, 1288–1299(1965).

Veselova et al, Luminescent properties of exciplexes of phthalimide derivatives with tetramethylidiaminodiphenylmethane, Opt. Spectstroc., vol. 42, No. 1., 1977,39–43.

Lakowicz et al, Theory of Phase-Modulation Fluorescence Spectroscopy For Excited-State Processes, Biophysical Chem 16(1982 99–115).

Lakowicz et al, Analysis of Excite-State Processes by Phase-Moduation Fluorescence Spectroscopy, Biophysical Chem 16 (1982) 117–132.

Bright, Frank V., A New Fiber-Optic-Based Multifrequency Phase-Modulation Fluorometer, Applied Spectroscopy, vol. 42, No.8, 1988,1531–1537.

Lakowicz et al, Detection of the Reversibility of an Excited-State Reaction by Phase-Modulation Fluorometry, Chemical Physics Letter, vol. 92, No. 2, 1982,117–121.

Sharma et al, Fiberoptic Oxygen Sensor Based on Fluorescence Quenching and Energy Transfer, Applied Spectroscopy, vol. 42, No. 6, 1988.

Lee et al, Luminescence Ratio Indicators for Oxygen, Anal. Chem., 1987, 59, 279–283.

Birks, Photophysics of Aromatic Molecules, 1970.

Lippitsch et al, Fibre-Optic Oxygen Sensor with the Fluorescence Decay Time as the Information Carrier, Anal. Chimica Acta, 205(1988)1.

Merlo et al, Development of a Fluorescence-Based Fiber Optic Sensor for Rapid Detection of General Anesthetics and Other Lipid-Soluble Chemicals, Ultrasonic and Optical Sensors.

Fig. 1

SENSING ELEMENTS AND METHODS FOR MAKING AND USING SAME

This application has been filed under 37 CFR § 1.47(a) and retains that status.

BACKGROUND OF THE INVENTION

The present invention relates to sensing or determining the concentration of an analyte in a medium. More particularly, the invention relates to a sensor and to a method for making a sensor and using a sensor for sensing the concentration of an analyte, for example, a gaseous component of interest, such as oxygen, in a medium, for example, blood.

It is sometimes necessary or desirable for a physician to determine the concentration of certain gases, e.g., oxygen and carbon dioxide, in blood. This can be accomplished utilizing an optical sensor which contains an optical indicator responsive to the component of interest. The optical sensor is exposed to the blood, and excitation light is provided to the sensor so that the optical indicator can provide an optical signal indicative of a characteristic of the analyte or component of interest. For example, the optical indicator may fluoresce and provide a fluorescent optical signal as described in Lubbers et al U.S. Pat. No. RE31,897 or it may function on the principals of light absorbance as described, for example, in Fostick U.S. Pat. No. 4,041,932.

The indicator material is often physically combined with a highly gas permeable matrix material, such as a polymeric matrix material, which is used to support the indicator material as it is exposed to the analyte. By "highly analyte permeable" is meant a material which is permeable to the analyte, in particular the gas of interest, and reaches equilibrium with the surrounding environment, which is at ambient temperature and atmospheric pressure, with respect to the analyte in a period of time measured in minutes or shorter time intervals rather than hours or longer time intervals.

One problem which has presented itself in the use of such sensors is the loss of indicator material. Thus, after a period of time in use, the amount of indicator material physically combined with the matrix material is reduced and may be leached into the medium. It would be advantageous to provide a gas sensor in which the indicator had a reduced tendency to escape from the matrix material.

Another problem which is often evident is the relatively low solubility of the indicator material in the matrix material. This feature limits the amount of indicator material that can be physically combined with the matrix material. In turn, the signal produced from the indicator/matrix material combination has a reduced intensity because of the relatively reduced amount of indicator material present. Clearly it would be advantageous to include increased amounts of indicator in the matrix material.

Yafuso et al U.S. Pat. No. 4,798,738 discloses chemically attaching ionic component sensitive dye to attachment sites on a water insoluble ionic permeable hydrophilic polymer. This allows the ionic component, e.g., pH, sensor to be constructed in the size domain of an optical fiber. Gas sensors are not disclosed.

SUMMARY OF THE INVENTION

New systems for sensing an analyte have been discovered. These new systems are based, in part, on the discovery that advantageous results are achieved by covalently attaching or bonding one or more analytes, for example, gas, sensitive indicator components or moieties to a matrix material, preferably a highly gas permeable polymeric matrix material and more preferably an addition cure silicone matrix material. Overall, such covalently attached analyte sensitive indicator components are substantially more effective than similar indicators which are physically admixed with the matrix material. For example, covalently bonding the indicator to the matrix material does not substantially interfere with its indicating properties. In addition, covalent bonding does provide for a more durable sensor. That is, the covalently bonded indicator component is more resistant to migration from the matrix material and the sensor into other components of the sensor system or into the medium being sensed. An additional beneficial feature of this invention is that the amount of indicator component to be included in the matrix material is not limited by physical considerations, such as the solubility of the indicator component in the matrix material. Thus, a predetermined, relatively large, amount of indicator component can be covalently bonded to the matrix material to give the desired signal in response to the concentration of analyte, preferably gaseous component, of interest in the medium. In other words, a relatively large amount of indicator component can be covalently bonded to a matrix material to provide a signal which is relatively easily measured to provide a basis for determining the concentration of the analyte of interest.

One broad aspect of the invention involves sensors for sensing an analyte, preferably the concentration of a gas, in a medium, preferably a liquid medium and more preferably blood. In one embodiment, the sensor comprises a sensing element including a matrix material, preferably a polymeric matrix material, more preferably a highly gas permeable polymeric matrix material, having at least one indicator component covalently bonded thereto. This indicator component is capable of providing a signal which is analyte sensitive, for example, dependent on the concentration of the analyte of interest in the medium. A transmission means, which is associated with the sensing means, is preferably included and acts to transmit the signal from the covalently bonded indicator component.

The indicator component is derived from at least one indicator substance or compound having an aromatic ring to which is directly covalently bonded a group including a functional portion which is conjugated relative to this aromatic ring. As used herein, the term "conjugated" means that the functional portion of the group includes or is directly bonded to that atom of such group which is directly covalently bonded to the indicator substance or compound, that is to an aromatic ring of the indicator substance or compound. Such "conjugated" indicator component precursors are illustrated by the following formula where IC is an aromatic indicator such as a polynuclear aromatic compound; and each R' is independently selected from H, monovalent hydrocarbyl radicals and substituted monovalent hydrocarbyl radicals. One of the carbon atoms bonded by the functional carbon-carbon double bond (the functional portion of the group attached to the aromatic indicator compound) is also bonded directly to the aromatic indicator compound, in particular to an aromatic ring of the indicator compound. Thus, the functional portion of the group attached to the aromatic indicator compound, that is the carbon-carbon double bond in the illustrated embodiment, is conjugated relative to the aromatic indicator compound, in particular to an aromatic ring of the indicator compound to which it is directly bonded. If one or more atoms are located in the chain between the functional carbon-carbon double bond and the aromatic ring of the aromatic indicator compound, then the functional carbon-carbon double bond would be isolated from this aromatic ring. Such materials including isolated functional portions are not within the scope of the present invention.

The use of groups including one or more conjugated (rather than isolated) functional portions often reduces the size of the groups, and allows for more effective and efficient production of indicator component precursor including such groups. Moreover, it has been found that little or no need exists to use isolated functional portions, for example, isolated multiple bonds, with relatively large attachment groups or linker arms to provide for increased indicator solubility or to minimize steric interaction between the dye and the polymer. The presently useful groups with conjugated functional portions provide sufficient indicator solubility so that the final sensing element is not restricted in indicator component content by the low inherent solubility of the indicator substance or compound in the matrix material or matrix material precursor, which often exists.

In another broad aspect, the invention is directed to methods for sensing the concentration of an analyte, preferably a gas, of interest in a medium, such as described above. In one embodiment, this method comprises exposing a sensing element, such as described above, to the medium, causing the indicator component to provide a signal dependent on, preferably a signal indicative of, the concentration of the analyte of interest in the medium, and analyzing this signal in determining the concentration of the analyte of interest in the medium.

A further broad aspect of the invention involves methods for producing a sensing element useful for sensing the concentration of an analyte, for example, a gaseous component, in a medium. In one embodiment, this production method comprises contacting a precursor of at least one indicator component with a polymer or a precursor of a polymer at conditions effective to form a polymeric matrix material having the indicator component covalently bonded thereto. The precursor of the indicator component is produced from an indicator compound having an aromatic ring to which is covalently bonded a group including a functional portion which is conjugated relative to the aromatic ring.

As used herein, the term "indicator component" means that moiety or entity which is chemically bonded to the matrix material and which provides a signal, for example, in response to or dependent on the concentration of the analyte of interest, preferably a signal which is indicative of the concentration of an analyte, e.g., a gas, of interest, in a medium. In effect, the indicator component is an integral part of the matrix material. This is contrasted with sensing elements in which the signal-producing indicator material is a separate chemical entity, for example, a separate indicator substance or compound, physically admixed with the matrix material.

In many instances, such separate indicator substances or compounds are not suitable to be covalently bonded to the matrix material. In these instances, it may be necessary to derivatize or functionalize such indicator substance or compound and produce a precursor of the indicator component. This is done by chemically modifying the indicator substance or compound, for example, such compound which includes an aromatic ring, to include at least one group having a conjugated functional portion, preferably a conjugated multiple bond, for example, conjugated relative to an aromatic ring of the indicator compound, capable of chemically reacting with the matrix material or precursor of the matrix material to covalently bond the indicator component thereto.

The functionalizing of the indicator substance or compound is illustrated by selecting a matrix material comprising a silicone-based polymer and an indicator substance which is a polynuclear aromatic compound. Such polynuclear aromatic compounds include the basic (underivatized) polynuclear aromatic compounds, as well as one or more derivatives thereof, that is one or more derivatives including non-functional groups which do not react with the matrix material or matrix material precursor. Such indicator substances or compounds are not able to be covalently bonded to such silicone-based polymers or their precursors. However, these indicator substances can be reacted to form attachment groups with conjugated multiple bonds, preferably conjugated carbon-carbon double bonds, which are capable of reacting with and bonding to silicone-based polymers and/or precursors thereof, such as polymethylhydrosiloxanes. In particular, if the silicone-based polymer is to be derived by addition curing, it is preferred to functionalize or derivatize the indicator substance or compound to attach one or more appropriately configured alkenyl groups and/or substituted alkenyl groups thereto. Such alkenyl and substituted alkenyl groups are capable of being hydrosilylated with a polymethylhydrosiloxane to covalently bond the indicator component to the silicone-based polymer precursor. The resulting precursor or compound can be cross-linked with vinyl terminated polysiloxane, thereby forming an addition-cure silicone including a covalently bonded analyte-sensitive indicator component.

Any type of functional group may be attached to the indicator substance or compound, provided that such group includes a functional portion, preferably a multiple bond, more preferably a carbon-carbon multiple bond and still more preferably a carbon-carbon double bond, which is conjugated relative to the indicator substance or compound, preferably conjugated relative to an aromatic ring of the indicator substance or compound, and is capable of chemically reacting with a polymer or polymer precursor to form the covalently bonded indicator component. The attached group should also have no substantial detrimental effect on the analyte sensitivity of the indicator component or on the medium to which the indicator component is exposed. Preferably, the group is organic in nature.

As noted above, particularly useful groups include groups, preferably alkenyl groups, with conjugated carbon-carbon double bonds; substituted groups, preferably substituted alkenyl groups, with conjugated double bonds and the like. Such groups preferably include 2 to about 20 carbon atoms. To illustrate, the preferred groups include, but are not limited to, where each $R^1$ is independently selected from H, monovalent hydrocarbyl radicals and substituted monovalent hydrocarbyl radicals, provided that the total number of carbon atoms is in the range of 2 to about 20. Also, two or more of the $R^1$s can be bonded together in a ring structure. Each $R^1$ is preferably independently selected from H, aliphatic monovalent hydrocarbyl radicals and substituted aliphatic monovalent hydrocarbyl radicals, more preferably from H, alkyl radicals and substituted alkyl radicals. More preferably, the group includes only one functional carbon-carbon bond. Examples of useful alkenyl groups include ethenyl (vinyl), propenyl, butenyl, hexenyl, heptenyl, octenyl, decenyl and the like groups wherein the carbon-carbon double bond is located so as to be conjugated relative to the indicator substance or compound. The presently useful substituted groups include the groups described herein substituted with one or more substituent groups including elements such as oxygen, nitrogen, carbon, hydrogen, silicon, halogen, phosphorus and the like and mixtures and combinations thereof. Thus, the attached group can include at least one heteroatom. In a particular useful embodiment, the attached group is a vinyl group. Very useful results are obtained with the indicator compound being selected from vinyl benzo[ghi]perylenes and mixtures thereof.

Various chemical modification techniques, many of which are conventional and well known in the art, may be employed to functionalize or derivatize the indicator substance with the group or groups to produce the indicator component precursor. Care should be exercised to avoid destroying or even substantially diminishing the analyte sensitivity (e.g., to the gas component of interest) of the indicator substance in the process of attaching one or more groups. However, it has been found that sufficient sensitivity is maintained if the characteristic structure of the indicator substance remains substantially unaffected, i.e., intact, after the chemical modification.

In a particularly useful embodiment, the indicator substance is sensitive to the concentration of oxygen and is one or more polynuclear aromatic compounds and/or one or more derivatives thereof. The basic polynuclear aromatic compound is preferably any fluorescent or absorbent, more preferably fluorescent, optical indicator of the polynuclear aromatic class. The polynuclear aromatic compound from which the indicator component is derived is still more preferably selected from the group consisting of perylene, derivatives of perylene, decacyclene, derivatives of decacyclene, benzoperylene, for example, benzo[ghi]-perylene, derivatives of benzoperylene, for example, derivatives of benzo[ghi]perylene, coronene, derivatives of coronene and mixtures thereof.

If desired, the basic polynuclear aromatic compound may be derivatized with one or more other groups, e.g., non-functional substituent groups such as alkyl groups.

Such de discussed in Yafuso et al U.S. Pat. No. 4,849,172 which is hereby incorporated in its entirety be reference herein. One goal of the use of such derivatives is to increase the solubility of the indicator substance in the matrix material. The "covalent bonding" feature of the present invention mitigates agains this solubility constraint. Thus, the basic or underivatized polynuclear aromatic compounds, e.g., as described herein, may be advantageously used to produce the indicator component.

In another useful embodiment, the sensing element further comprises at least one additional indicator component covalently bonded to the matrix material. The additional indicator component may be derived in much the same way that the indicator component is. For example, an additional indicator substance or compound may be derivatized to include a covalently bonded group having a functional portion which is conjugated relative to the additional indicator substance, for example, conjugated relative to an aromatic ring of the additional indicator substance or compound. This additional indicator component is capable of providing an additional signal which is substantially independent of, or has substantially reduced sensitivity to, the analyte, for example, the gas of interest, in the medium to which the indicator component is sensitive. The transmission means preferably acts to transmit this additional signal from the additional indicator component. By comparing, e.g., ratioing, the signal from the indicator component and the additional signal from the additional indicator component, one can improve the accuracy of the analyte concentration determination. For example, such comparing reduces, or even eliminates, the detrimental effects on concentration determination accuracy caused by, for example, fluctuations in the signal or signals used to excite the sensing element, and signal transmission losses from physically bending the transmission means, e.g., an optical fiber or the like or a substantially equivalent element useful for transmitting signals from the indicator component and/or additional indicator component.

If an indicator component and an additional indicator component are to be used, one preferred combination is an indicator component derived from benzo[ghi]perylene, derivatives of benzo[ghi]perylene and mixtures thereof, and an additional indicator component derived from perylene, derivatives of perylene and mixtures thereof.

Any suitable matrix material, preferably a polymeric matrix material, may be employed provided that it functions as described herein. Particularly useful polymeric matrix materials include those based on addition cure silicone polymers. The matrix material, or the precursor thereof, should be such as to chemically react with the precursor or precursors of the indicator component and produce a sensing element with covalently bonded indicator component.

Although various polymers can be employed as the matrix material, it is preferred that the matrix material be permeable, preferably highly permeable, to the analyte, for example, gas, of interest so that the sensitivity of the indicator component to the analyte of interest is optimized. If a silicone-based polymer is employed in the matrix material, it may include polymers derived from vinyl terminated polysiloxanes and polyalkyl(phenyl)hydrosiloxanes, herein referred to as polymethylhydrosiloxanes. Such polymethylhydrosiloxanes include, but are not limited to, those having the formula where m is an integer of from 1 to 500 and R is independently selected from the group consisting of H, alkyl and substituted alkyl, preferably $CH_3$, $CH_2CH_2CF_3$ and $CH_2(CH_2)nCH_3$, and phenyl, where n is an integer from 1 to 22. Of this group, polymers in which a major portion of the R groups are methyl are preferred because of the high gas permeability of such polymers. It is of course realized that other members of the homologous series which include the above-noted polymers may also be used. The final silicone-based matrix material is cross-linked. Suitable vinyl terminated polysiloxanes include two or more functional vinyl groups which react with the hydride or hydro groups of the polymethylhydrosiloxanes to form the cross-linked matrix material. Such cross-linking advantageously occurs in the presence of a catalyst, such as a platinum-containing catalyst. The properties of the cross-linked silicone can be varied by changing the degree of cross-linking, for example, by adjusting the concentration of the Si—H groups on the polymethylhydrosiloxanes and/or the molecular weight of the vinyl-terminated polysiloxanes.

An optical sensor constructed in accordance with the teachings of this invention preferably has a higher concentration of the indicator component in the polymeric matrix relative to the concentration of a non-covalently bonded indicator substance or compound which is physically mixed in a matrix material and, as a result thereof, the output signal intensity or strength obtainable from the indicator component is also relatively higher.

The precursors of the indicator components useful in the present invention can be obtained using one or more of a variety of synthesizing procedures, such as a Friedel-Craft or Vilsmeier reaction followed by a Wittig reaction. The indicator component precursor or precursors can be dispersed in a silicone-based polymer, such as polymethylhydrosiloxane, in a volatile solvent, such as benzene, hexane and the like, and be allowed to react to covalently bond the indicator component or components to the silicone-based polymer. The silicone-based polymer, having the chemically attached indicator component or components, is then reacted, for example, using conventional addition curing, to form the sensing element.

An alternative method for producing the present sensing element involves combining the precursor or precursors of the indicator component or components with the vinyl terminated polysiloxane, preferably in an inert solvent to promote dissolution of the above-noted precursor or precursors, and any catalyst e.g., platinum group metal, which may be employed. This combination is then mixed with the polymethylhydrosiloxane at conditions effective to simultaneously covalently bond the indicator component or components to the matrix material and form the present sensing element. These alternatives have been found to be effective in increasing the degree to which the indicator component or components is covalently bonded to the matrix material.

These and other aspects and advantages of the present invention are set forth in the following detailed description and claims, particularly when considered in conjunction with the accompanying drawing.

DETAILED DESCRIPTION OF THE DRAWING

Figure 1:
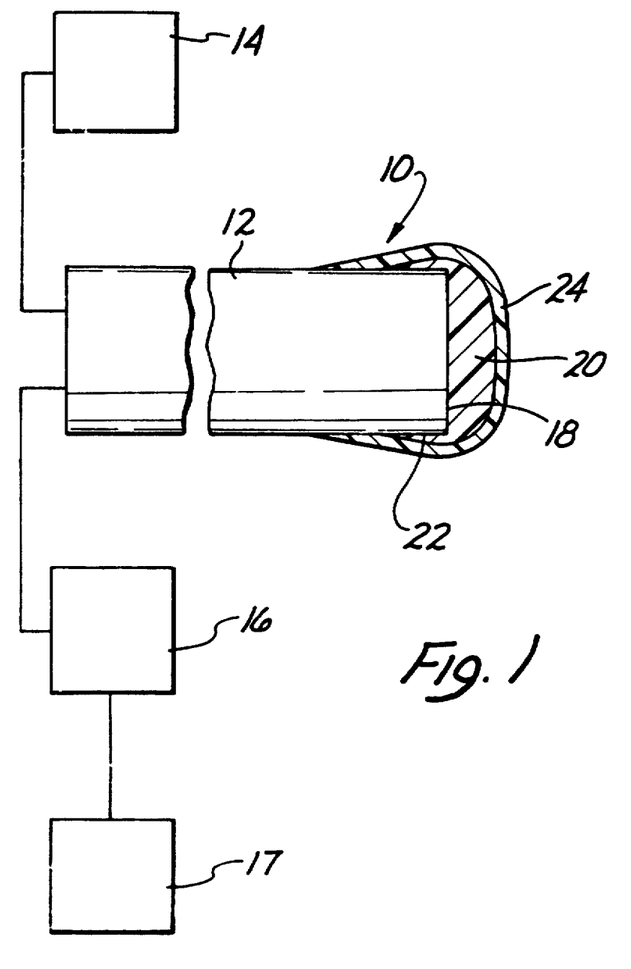
FIG. 1 is a schematic illustration of a sensor apparatus according to the present invention.

FIG. 1 shows a sensor 10 according to the present invention. Sensor 10 is adapted to determine the concentration or partial pressure of oxygen in blood. An optical fiber 12 is connected to an appropriate light transmitting apparatus 14, which is capable of transmitting light at 395 nanometers and at 425 nanometers. The light transmitting apparatus 12 generates the excitation light at these two wavelengths. The optical fiber 12 is also connected to a light receiving apparatus 16, which, in turn, is connected to a conventional electronic processor 17.

Located on the optical surface 18 of the optical fiber 12 is a matrix 20 which is a highly oxygen permeable material, such as a cross-linked, siloxane-based polymer. Matrix 20 includes about 1.0% by weight of an indicator component derived from vinyl benzo[ghi]perylene covalently bonded to the polymer and about 1.0% by weight of vinyl perylene covalently bonded to the polymer.

The matrix 20 adheres to the optical surface 18 and slightly down along the sides 22 of the end of fiber 12. An opaque overcoating 24, comprising a mixture of carbon black and cellulosic material, can then be applied over the totality of the matrix 20 and down further along the side 22 of the fiber 12.

In use, sensor 10 functions as follows. The tip of optical fiber 12 including matrix 20 and overcoating 24 is exposed or immersed in blood, the oxygen concentration of which is to be determined. Light transmitting apparatus 14 transmits light at 395 nanometers to the optical fiber 12. The excitation light at 395 nanometers causes the benzo[ghi]perylene functionality in matrix 20 to fluoresce. The lifetime of this fluorescent signal, at a wavelength of about 450 nanometers, is longer than about 50 nanoseconds. A fluorescent signal is transmitted from matrix 20 through optical fiber 12 to light receiving apparatus 16. This fluorescent signal, derived from excitation light at 395 nanometers, depends on the concentration of oxygen in the blood being analyzed. Processor 17 uses information received by light receiving apparatus 16 on this fluorescent signal to determine a preliminary value of the oxygen concentration in the blood. Receipt and analysis of this fluorescent light by light receiving apparatus 16 and processor 17 is carried out in a manner similar to that described in the above-referenced Lubbers, et al patent and in Heitzmann U.S. Pat. No. 4,557,900, each of which is incorporated in its entirety herein by reference.

Light transmitting apparatus 14 then transmits light at 430 nanometers to the optical fiber 12. The excitation light at 430 nanometers causes the perylene functionality in matrix 20 to fluoresce. The lifetime of this fluorescent signal, at a wavelength of about 450 nanometers, is shorter than about 5 nanoseconds. A fluorescent signal is transmitted from matrix 20 through optical fiber 12 to light receiving apparatus 16. This fluorescent signal, derived from excitation light at 430 nanometers, is only weakly responsive to the concentration of oxygen in the blood being analyzed. Processor 17 uses information received by light receiving apparatus 16 of this fluorescent signal to develop a ratio of the fluorescent signal derived from excitation at 395 nanometers to the fluorescent signal derived from excitation at 430 nanometers. Using this ratio together with the above-noted preliminary oxygen concentration, processor 17 determines a corrected or final concentration of oxygen in the blood to be analyzed. This corrected oxygen concentration is found to be accurate even if the optical fiber 12 is bent at one or more points along its length and/or if other light transmission difficulties are encountered.

The above-noted procedure may occur periodically or even substantially continuously to give substantially continuous oxygen concentration results. Of course, the excitation at 430 nanometers can take place before excitation at 395 nanometers. Also, by proper selection of the optical indicator components, the concentration of other gaseous components of interest can be determined. In addition, media other than blood can be analyzed.

The optical fiber 12 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of oxygen concentration in the blood.

Over time, the sensor 10 maintains its ability to sense the concentration of oxygen in the blood. The covalently bonded benzo[ghi]perylene functionality and perylene functionality remain in matrix 20 and are not leached into the blood. Also, the relatively large amounts of such functionalities in matrix 20 provide for intense signals which are easily measured. This, in turn, facilitates increased accuracy in measuring oxygen concentrations.

The following non-limiting Examples illustrate certain aspects of the invention.

EXAMPLE 1

Into a clean dry 500 ml round-bottom flask fitted with a drying tube, a rubber septum and a magnetic stirrer was added 3.2 g of benzo[ghi]perylene and 400 ml of dichloromethane under a blanket of dry nitrogen. When the crystals had dissolved, the solution was cooled to 10° C. Using a 10 ml syringe, 7.5 g of tin (IV)tetrachloride was added. The mixture was made homogenous by stirring, then 4.5 g of dichloromethyl methyl ether was added over 2 minutes. The mixture became blue purple and viscous. The viscosity dropped after about 30 minutes of stirring. The reaction was complete after about 150 minutes. The reaction mixtures was quenched with 600 ml of 2N HCl and the product extracted with 600 ml of dichloromethane. The organic layer was washed with 600 ml of water and dried over anhydrous sodium sulfate. The organic phase was passed through a 3.5"×2" silica gel plug, and the product, benzo[ghi]perylene aldehyde in good yield and purity, was separated from the solvent with a rotary evaporator.

EXAMPLE 2

2.7 g of methyl iodide and 4.5 g of 4-(diisopropylaminomethyl)triphenyl phosphine in 10 ml of toluene were allowed to react in a 50 ml round-bottom flask equipped with a magnetic stirrer with stirring overnight at room temperature under dry nitrogen. The reaction mixture formed two phases. The toluene was removed by rotary evaporation. To the remaining mixture was added 12 mmoles of lithium diisopropyl amide in anhydrous tetrahydrofuran at 0° C. and stirred for 30 minutes at this temperature. This mixture was added to 3.1 g of benzo[ghi]perylene aldehyde dissolved in 300 ml of anhydrous tetrahydrofuran under an inert atmosphere (dry nitrogen or argon) at 0° C. The reaction was over in an hour, at which time the solvent was removed by rotary evaporation. The residue was dissolved in 500 ml of toluene and washed with 2, 100 ml portions of 0.50M HCl followed by a water wash and an aqueous 2.5% sodium bicarbonate wash. The organic phase was dried over sodium sulfate. The dry organic phase was stirred with 2 g of activated charcoal, then chromatographed on a 3"×1" silica gel column that had been deactivated with ethanol. The product was eluted from the column with toluene. The product, a mixture of vinyl benzo[ghi]perylene isomers, was recovered by rotary evaporation of the solvent and stored in an amber bottle under nitrogen.

EXAMPLE 3

In a 50 ml round-bottomed flask equipped with a magnetic stirrer was placed the vinyl benzo[ghi]perylene product from Example 2 (100 mg), polymethylhydrosiloxane (sold by Petrarch Systems under the trademark PS 123), and benzene (10 ml). Platinum catalyst (sold by Petrarch Systems under the trademark PC 072) diluted in hexanes (10 microliters of 0.125% Pt in hexanes), was added at room temperature. The mixture was warmed to 60° C. for 30 minutes. The reaction was determined to be complete by thin layer chromatography (no fluorescent material eluted by hexanes on silica gel, all fluorescent material adhered to the baseline). Decolorizing carbon particles, sold by J. T. Baker Chemical Company under the trademark Darco G-60, (400 mg) was added and the mixture was stirred two hours, and then filtered through celite. The benzene was removed by rotary evaporation and replaced by hexane. This mixture was then combined with vinyl terminated siloxanes and allowed to react to form a cross-linked fluorescent silicone rubber.

The resulting cross-linked fluorescent silicone rubber includes an effective amount of chemically bound, non-leachable benzo[ghi]perylenyl moiety, and is effective as a sensing element in an in vivo blood oxygen sensor.

While this invention has been described with respect to various specific examples and embodiments, it is to be understood that the invention is not limited thereto and that it can be variously practiced within the scope of the following claims.

What is claimed is:

1. A sensing element for sensing the concentration of an analyte in a medium comprising:
   a matrix material having at least one indicator component covalently bonded thereto, said indicator component being capable of providing a signal dependent on the concentration of an analyte in a medium and being derived from at least one indicator compound having an aromatic ring to which is directly covalently bonded a group including a functional portion which is conjugated relative to said aromatic ring.

2. The sensing element of claim 1 wherein said at least one indicator compound is a polynuclear aromatic compound.

3. The sensing element of claim 2 wherein said polynuclear aromatic compound is selected from decacyclene, derivatives of decacylene, perylene, derivatives of perylene, benzo[ghi]perylene, derivatives of benzo[ghi]perylene, coronene, derivatives of coronene and mixtures thereof.

4. The sensing element of claim 1 wherein said functional portion is a multiple bond which includes an atom to which said aromatic ring is directly covalently bonded.

5. The sensing element of claim 4 wherein said group is a vinyl group.

6. The sensing element of claim 4 wherein said at least one indicator compound is selected from the group consisting of vinyl benzo[ghi]perylenes and mixtures thereof.

7. The sensing element of claim 1 wherein said functional portion is a carbon-carbon double bond.

8. The sensing element of claim 1 wherein said matrix material is a polymeric matrix material which is highly permeable to said analyte.

9. The sensing element of claim 8 wherein said polymeric matrix material is a silicone-based polymeric material.

10. The sensing element of claim 1 wherein said analyte is oxygen.

11. A method for sensing the concentration of an analyte in a medium comprising:
exposing a sensing element to said medium, said sensing element comprising a matrix material having at least one indicator component covalently bonded thereto, said indicator component being capable of providing a signal dependent on the concentration of said analyte in said medium and being derived from at least one indicator compound having an aromatic ring to which is directly covalently bonded a group including a functional portion which is conjugated relative to said aromatic ring;
causing said indicator component to provide said signal; and
analyzing said signal in determining the concentration of said analyte in said medium.

12. The method of claim 11 wherein said at least one indicator compound is a polynuclear aromatic compound.

13. The method of claim 12 wherein said polynuclear aromatic compound is selected from decacyclene, derivatives of decacylene, perylene, derivatives of perylene, benzo[ghi]perylene, derivatives of benzo[ghi]perylene, coronene, derivatives of coronene and mixtures thereof.

14. The method of claim 11 wherein said functional portion is a multiple bond which includes an atom to which said aromatic ring is directly covalently bonded.

15. The method of claim 14 wherein said functional portion is a carbon-carbon double bond.

16. The method of claim 14 wherein said group is a vinyl group.

17. The method of claim 14 wherein said at least one indicator compound is selected from the group consisting of vinyl benzo[ghi]perylenes and mixtures thereof.

18. The method of claim 11 wherein said matrix material is a polymeric matrix material which is highly permeable to said analyte.

19. The method of claim 18 wherein said polymeric matrix material is a silicone-based polymeric material.

20. The method of claim 11 wherein said analyte is oxygen.

21. A method for producing a sensing element useful for sensing the concentration of an analyte in a medium comprising:
contacting at least one precursor of an indicator component with a reactable material at conditions effective to form a matrix material having said indicator component covalently bonded thereto, said at least one precursor of said indicator component including an indicator compound having an aromatic ring to which is directly covalently bonded a group including a functional portion which is conjugated relative to said aromatic ring and which is capable of chemically reacting at said conditions, said covalently bonded indicator component being capable of providing a signal dependent on the concentration of said analyte in said medium.

22. The method of claim 21 wherein said indicator compound is a polynuclear aromatic compound.

23. The method of claim 21 wherein said polynuclear aromatic compound is selected from decacyclene, derivatives of decacylene, perylene, derivatives of perylene, benzo[ghi]perylene, derivatives of benzo[ghi]perylene, coronene, derivatives of coronene and mixtures thereof.

24. The method of claim 21 wherein said functional group is a multiple bond which includes an atom to which said aromatic ring is directly covalently bonded.

25. The method of claim 24 wherein said functional portion is a carbon-carbon double bond.

26. The method of claim 24 wherein said group is a vinyl group.

27. The method of claim 24 wherein said at least one precursor of said indicator component is selected from the group consisting of vinylbenzo[ghi]perylenes and mixtures thereof.

28. The method of claim 21 wherein said matrix material is a polymeric matrix material which is highly permeable to said analyte.

29. The method of claim 28 wherein said polymeric matrix material is a silicone-based polymeric material.

30. The method of claim 21 wherein said analyte is oxygen.

31. A method for producing a sensing element useful for sensing the concentration of an analyte in a medium comprising:
contacting a composition containing at least one precursor of an indicator component and at least one of a silicone-based polymer and a precursor of a silicone-based polymer at conditions effective to form a cross-linked, silicone-based polymeric matrix material having said indicator component covalently bonded thereto, said covalently bonded indicator component being capable of providing a signal dependent on the concentration of said analyte in said medium, said at least one precursor of said indicator component including an indicator compound having an aromatic ring to which is covalently bonded a group including a functional portion which is conjugated relative to said aromatic ring and which is capable of chemically reacting at said conditions.

32. The method of claim 31 wherein said at least one indicator compound is a polynuclear aromatic compound.

33. The method of claim 32 wherein said polynuclear aromatic compound is selected from decacyclene, derivatives of decacylene, perylene, derivatives of benzo[ghi]perylene, derivatives of benzo[ghi]perylene, coronene, derivatives of coronene and mixtures thereof.

34. The method of claim 31 where in said functional portion is a multiple bond which includes an atom to which said aromatic ring is directly covalently bonded.

35. The method of claim 34 wherein said functional portion is a carbon-carbon double bond.

36. The method of claim 34 wherein said group is a vinyl group.

37. The method of claim 34 wherein said at least one precursor of said indicator component is selected from the group consisting of vinyl benzo[ghi]perylene and mixtures thereof.

38. The method of claim 31 wherein said analyte is oxygen.

39. The method of claim 31 wherein said group includes a heteroatom.

* * * * *

UNITED STATES PATENT AND TRADEMARK OFFICE
CERTIFICATE OF CORRECTION

PATENT NO. : 5,296,381
DATED : March 22, 1994
INVENTOR(S) : Yafuso et al It is certified that error appears in the above-identified patent and that said Letters Patent is hereby corrected as shown below:

Column 2, line 64 after "indicator" insert -- compound --.

Column 2, line 65 change "R'" to -- $R^1$ --.

Column 6, line 1 change "de" to -- derivatives are --.

Column 6, line 6 change "agains" to -- against --.

Column 11, line 17 change "1" to -- 4 --.

Signed and Sealed this

Fourteenth Day of March, 1995

*Attest:*

BRUCE LEHMAN

*Attesting Officer*    *Commissioner of Patents and Trademarks*